(12) United States Patent
Alvarez (10) Patent No.: US 12,226,222 B2
(45) Date of Patent: *Feb. 18, 2025

(54) WIRELESS ACTIVE MONITORING IMPLANT SYSTEM

(71) Applicant: Hologic, Inc., Marlborough, MA (US)

(72) Inventor: Estefania Alvarez, West Newton, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/464,441

(22) Filed: Sep. 11, 2023

(65) Prior Publication Data

US 2024/0065614 A1    Feb. 29, 2024

Related U.S. Application Data

(63) Continuation of application No. 16/647,293, filed as application No. PCT/US2018/050174 on Sep. 10, 2018, now Pat. No. 11,877,857.

(Continued)

(51) Int. Cl.
*A61B 5/00* (2006.01)
*A61B 5/1468* (2006.01)
(Continued)

(52) U.S. Cl.
CPC .......... *A61B 5/4312* (2013.01); *A61B 5/0022* (2013.01); *A61B 5/1468* (2013.01);
(Continued)

(58) Field of Classification Search
CPC ... A61B 5/4312; A61B 5/0022; A61B 5/1468; A61B 5/4842; A61B 5/4848;
(Continued)

(56) References Cited

U.S. PATENT DOCUMENTS

2002/0137991 A1    9/2002   Scarantino
2009/0171244 A1*   7/2009   Ning ................... A61B 6/0435
                                                         378/37
(Continued)

FOREIGN PATENT DOCUMENTS

CN   101455562         6/2009
CN   101455562 A   *   6/2009
(Continued)

OTHER PUBLICATIONS

Simonsen, Michael. "BB&T at the Society of Interventional Radiology Scientific Meeting: 1st of 2 parts." Biomedical Business & Technology : NA. AHC Media LLC. (Apr. 1, 2008) (Year: 2008).*

(Continued)

*Primary Examiner* — Linh Giang Le
(74) *Attorney, Agent, or Firm* — Merchant & Gould P.C.

(57) ABSTRACT

Examples of the present disclosure describe systems and methods for the long-term, real-time active monitoring of a wireless implant. In aspects, a wireless biosensor may be implanted in a breast biopsy cavity. The biosensor may detect biochemical parameter data of the breast biopsy cavity and the human body. The biosensor may transmit the detected biochemical parameter data in real-time to a surveillance system wirelessly coupled to the biosensor. The surveillance system may then facilitate the evaluation of the biochemical parameter data. In examples, the evaluation may comprise detecting trends in a tumor's microenvironment, monitoring the progress of a treatment, or adjusting a treatment to tailor a personalized treatment.

20 Claims, 5 Drawing Sheets

Related U.S. Application Data (60) Provisional application No. 62/558,034, filed on Sep. 13, 2017.

(51) Int. Cl.
  G16H 20/10 (2018.01)
  G16H 50/20 (2018.01)

(52) U.S. Cl.
  CPC .......... *A61B 5/4842* (2013.01); *A61B 5/4848* (2013.01); *A61B 5/6867* (2013.01); *A61B 5/74* (2013.01); *G16H 20/10* (2018.01); *G16H 50/20* (2018.01); *A61B 2560/0219* (2013.01)

(58) Field of Classification Search
  CPC . A61B 5/6867; A61B 5/74; A61B 2560/0219; A61B 5/14539; A61B 5/14542; A61B 5/14546; A61B 5/1473; A61B 5/4836; A61B 5/14503; G16H 20/10; G16H 50/20; G16H 40/67
  See application file for complete search history.

(56) References Cited

U.S. PATENT DOCUMENTS

| | | | |
|---|---|---|---|
| 2010/0256610 A1* | 10/2010 | Rigas | A61B 5/0031 604/891.1 |
| 2014/0194741 A1 | 7/2014 | Sirimanne | |
| 2015/0112194 A1 | 4/2015 | Stubbs | |
| 2015/0327989 A1 | 11/2015 | Boyden | |
| 2016/0007893 A1 | 1/2016 | Roberts | |
| 2016/0354177 A1 | 12/2016 | Rulkov et al. | |
| 2017/0181825 A1 | 6/2017 | Hunter | |
| 2020/0275878 A1 | 9/2020 | Alvarez | |

FOREIGN PATENT DOCUMENTS

| | | |
|---|---|---|
| CN | 104939843 | 9/2015 |
| EP | 2277553 | 1/2011 |
| JP | 2008-521576 | 6/2008 |
| JP | 2009-505793 | 2/2009 |
| JP | 2016-534824 | 11/2016 |
| JP | 2020-514710 | 5/2020 |
| WO | 00/18294 | 4/2000 |
| WO | 2007/027570 | 3/2007 |

OTHER PUBLICATIONS

European Communication and Search Report in Application 18855859.7, mailed Jul. 22, 2021, 8 pages.

PCT International Preliminary Report on Patentability in International Application PCT/US2018/050174, mailed Mar. 26, 2020, 13 pages.

PCT International Search Report and Written Opinion in International Application PCT/US2018/050174, mailed Dec. 31, 2018, 19 pages.

Simonsen, Michael, "BB&T at the Society of Interventional Radiology Scientific Meeting: 1st of 2nd parts", Biomedical Business & Technology, NA, AHC Media LLC, Apr. 1, 2008.

* cited by examiner

WIRELESS ACTIVE MONITORING IMPLANT SYSTEM

CROSS-REFERENCE TO RELATED APPLICATIONS

This application is a continuation of U.S. patent application Ser. No. 16/647,293, now U.S. Pat. No. 11,877,857, filed Mar. 13, 2020, which is a National Stage Application of PCT/US2018/050174, filed Sep. 10, 2018, which claims priority to U.S. Provisional Patent Application No. 62/558,034, filed Sep. 13, 2017, the disclosures of which are hereby incorporated by reference herein in their entireties. To the extent appropriate, a claim of priority is made to each of the above disclosed applications.

BACKGROUND

A key element in the management of breast cancer is monitoring the response to treatment. Currently, only external imaging and blood tests are used to assess the response to treatment. Such techniques, however, are deficient for various reasons. As one example, these techniques are only able to detect actual physical changes in the macroenvironment of a breast cancer tumor. As another example, these techniques rely on comparing recently-acquired images and data with previously-acquired images and data (which may not exist). As such, there is currently no means to monitor or evaluate real-time information on the effectiveness of breast cancer treatment.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for the active monitoring of a wireless implant. In aspects, a wireless biosensor may be implanted in a breast biopsy cavity. The biosensor may detect biochemical parameter data of the breast biopsy cavity and the human body. The biosensor may transmit the detected biochemical parameter data in real-time to a surveillance system wirelessly coupled to the biosensor. The surveillance system may then facilitate the evaluation of the biochemical parameter data. In examples, the evaluation may comprise detecting trends in a tumor's microenvironment, monitoring the progress of a treatment, or adjusting a treatment to tailor a personalized treatment.

Aspects of the present disclosure provide an implantable active detection system comprising: a site marker for deployment in a breast biopsy cavity, the site marker comprising: at least one processor; and memory coupled to the at least one processor, the memory comprising computer executable instructions that, when executed by the at least one processor, performs a method comprising: when implanted in the breast biopsy cavity, detecting data related to a human body in the breast biopsy cavity in real-time, wherein the data comprises one or more biochemical parameters; and transmitting the data to an external monitoring device.

Aspects of the present disclosure further provide a monitoring system comprising: at least one processor; and memory coupled to the at least one processor, the memory comprising computer executable instructions that, when executed by the at least one processor, performs a method comprising: receiving data collected in real-time from an implantable sensor coupled to a site marker implanted in a breast biopsy cavity of a human body, wherein the data comprises one or more biochemical parameters and respective values; and processing the data to determine one or more trends in the breast biopsy cavity.

Aspects of the present disclosure further provide an active monitoring implant system comprising: a site marker for deployment in a breast biopsy cavity, wherein the site marker is coupled to an implantable sensor configured to: when implanted in the breast biopsy cavity, detect data in the breast biopsy cavity in real-time, wherein the data comprises one or more biochemical parameters related to a human body; and a monitoring device external to the breast biopsy cavity, wherein the monitoring device is configured to: collect the data from the implantable sensor; and process the data to generate processed data.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

As of 2017, approximately 1 in 8 women in the U.S. will develop invasive breast cancer in their lifetimes. This results in approximately 225,000 new cases of invasive breast cancer being diagnosed annually. Of these cases, depending on the type and size of tumor, approximately 20-25% of patients undergo neoadjuvant chemotherapy in order to reduce tumor size and/or downstage nodal disease. Generally, neoadjuvant chemotherapy is performed over a period of 3 to 9 months. During this period, physicians rely on external still images and blood tests to evaluate the treatment of the tumor. However, these techniques are deficient for several reasons. For example, there are no randomized clinical trials to evaluate the effectiveness of external functioning imaging modalities (e.g., ultrasound, computed tomography (CT), positron emission tomography (PET), magnetic resonance imaging (MRI), mammogram, etc.) for breast cancer surveillance or tumor monitoring. As such, there is no definitive evidence to support the use of such imaging modalities as a primary means for surveillance and treatment response. Moreover, such imaging modalities provide for sporadic monitoring at a macroscopic level. Such macroscopic monitoring may be sufficient to identify physical and anatomical changes to a tumor by evaluating actual structural tissue changes, such as the dimensions of the lesion. However, such changes take considerably longer to detect than in situ changes that occur at a cellular level. Thus, as macroscopic monitoring is insufficient to provide continuous monitoring of the neoplastic microenvironment (e.g., at a cellular level within the tumor site), such monitoring does not enable the accurate calculation of a pathological response non-invasively.

As a result of physicians' reliance on external still images and blood tests, patients are forced to wait for follow-up appointments with their physicians to receive updates on the effectiveness of a treatment. This wait often leads to stress, anxiety, depression, and economic cost for patients during treatment. The psychological impact of such factors is an important aspect throughout treatment, as approximately ⅓ of breast cancer patients experience distress. Of these patients, approximately 70% consider a referral to a cancer support specialist. It is, thus, imperative to provide such patients with a more expeditious means of evaluating the effectiveness of treatment. Moreover, women that have a high risk of being diagnosed with breast cancer or have had breast cancer previously are reliant on annual or biannual mammography for diagnosis. These woman would also benefit from the expeditious and reliable detection of changes and abnormalities in their breast microenvironments.

Accordingly, the present disclosure describe systems and methods for the active monitoring of a wireless biosensor. In aspects, a wireless biocompatible sensor (biosensor) may be implanted next to, or in, a breast biopsy cavity percutaneously or in a minimally invasive manner. The biosensor may comprise, be comprised in, or be coupled to a permanent (or long-term) site marker. Site markers or breast biopsy markers have been used in the field of interventional radiology since 1980s. Such markers are manmade, millimeter-sized metal, polymer, or ceramic implants that are deployed using a trocar or a needle. Generally, these markers do not contain "smart" components or sensor components. A "smart" component, as used herein, may refer to a component capable of operating, to some extent, interactively and/or autonomously. Attributes such as material, shape, form, and composition define markers as non-anatomical structures that geographically mark the location of, for example, a breast biopsy site. The composition and shape of a marker enables the marker to be visualized in a variety of external imaging modalities, such as radiography, MRI, ultrasound, tomography, nuclear medicine, photoacoustic imaging, near-infrared (NIR) spectroscopy, tactile imaging, etc. Such visualization facilitates, among other things, the surgical removal of the marker, tumors and lesions around the marker. In examples, when implanted, the biosensor may detect data related to biochemical parameters of the breast biopsy cavity. The biosensor may also detect data related to biochemical parameters throughout the human body. Non-exhaustive examples of biochemical parameters include circulating tumor cells, circulating tumor DNA, proteins, serum soluble human epidermal growth factor receptor 2 (HER2)/neu oncogene, urokinase plasminogen activator (UPA) and plasminogen activator inhibitor-1 (PAI-1) biomarkers, oxygen levels; pH levels; nitric oxide and interstitial fluid pressure. Within the current literature, these are the most known biomarkers that have been analyzed and measured to understand cancer's stage and possible treatment. In some examples, the biosensor may be powered internally. In other examples, the biosensor may be powered externally using one or more wireless power transfer techniques.

In aspects, the biosensor may be wirelessly coupled to a surveillance system. The surveillance system may be, or may be implemented in, a mobile device. The surveillance system may receive or collect biochemical parameter data from the biosensor. In examples, the biochemical parameter data may be received/collected in real-time, periodically, on-demand or in response to the satisfaction of one or more criteria, as a sensor may be powered or inquired externally. The surveillance system may also transmit data and/or settings to the biosensor. For example, the surveillance system may specify or modify the biochemical parameters to be monitored by the biosensor, or transmit activation signals to the biosensor. In some aspects, the surveillance system may process the biochemical parameter data using a data processing component accessible to the surveillance system. In other aspects, the surveillance system may transmit the biochemical parameter data to an external processing system. In either aspect, the processed biochemical parameter data may be used to detect trends in a breast biopsy cavity, monitor the progress of a treatment, or adjust a treatment to tailor a personalized treatment.

Accordingly, the present disclosure provides a plurality of technical benefits including but not limited to: implanting a long-term biochemical parameter sensor in a minimally invasive manner; noninvasively monitoring biochemical parameter data in a biopsy cavity; noninvasively monitoring biochemical parameter data throughout a biological organism; collecting real-time data for a set of biochemical parameters; dynamically detecting trends indicating a tumor's response to treatment; evaluating changes to a neoplastic environment at a cellular level; personalizing treatments in real-time; reducing the psychological impact on cancer patients using dynamically-collected biosensor data.

Figure 1:
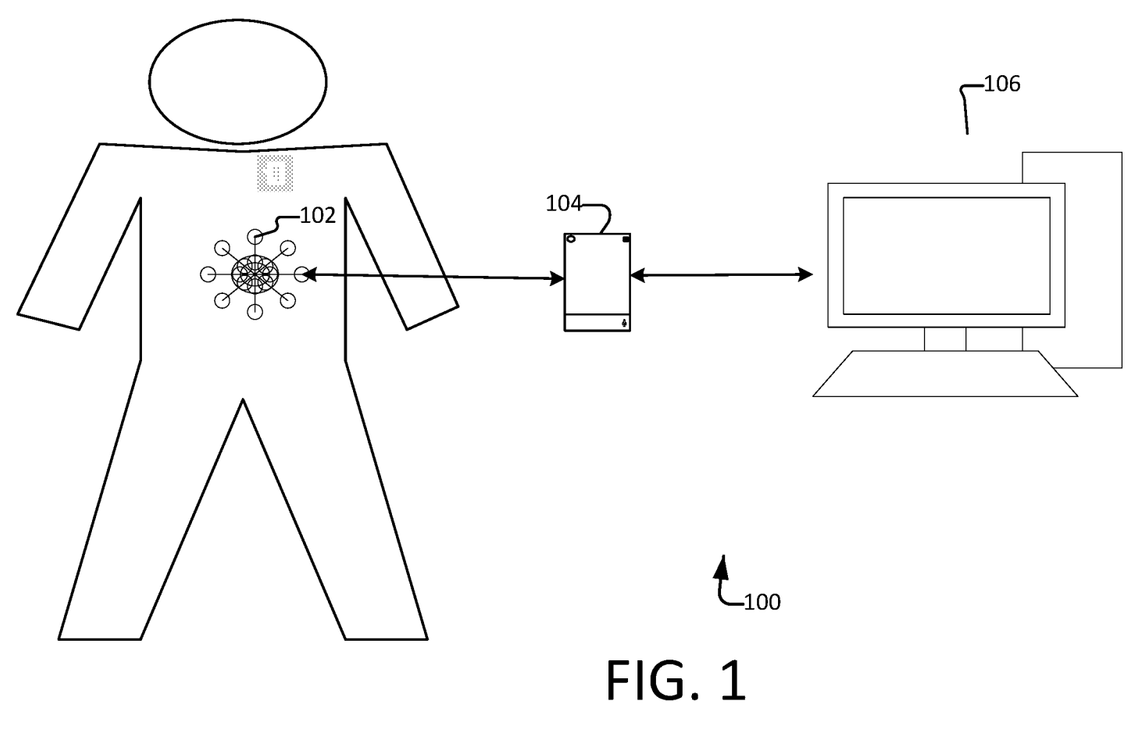
FIG. 1 illustrates an overview of an example system for the active monitoring of a wireless biosensor as described herein.

FIG. 1 illustrates an overview of an example system for the active monitoring of a wireless biosensor as described herein. Example system 100 presented is a combination of interdependent components that interact to form an integrated whole for venue detection systems. Components of the systems may be hardware components or software implemented on and/or executed by hardware components of the systems. In examples, system 100 may include any of hardware components (e.g., used to execute/run operating system (OS)), and software components (e.g., applications, application programming interfaces (APIs), modules, virtual machines, runtime libraries, etc.) running on hardware. In one example, an example system 100 may provide an environment for software components to run, obey constraints set for operating, and utilize resources or facilities of the system 100, where components may be software (e.g., application, program, module, etc.) running on one or more processing devices. For instance, software (e.g., applications, operational instructions, modules, etc.) may be run on a processing device such as a computer, mobile device (e.g., smartphone/phone, tablet, laptop, personal digital assistant (PDA), etc.) and/or any other electronic devices. As an example of a processing device operating environment, refer to the example operating environments depicted in FIG. 5.

In other examples, the components of systems disclosed herein may be spread across multiple devices. For instance, input may be entered on a client device and information may be processed or accessed from other devices in a network, such as one or more server devices.

As one example, the system 100 comprises sensor 102, surveillance system 104 and input processing system 106. One of skill in the art will appreciate that the scale of systems such as system 100 may vary and may include more or fewer components than those described in FIG. 1. In some examples, interfacing between components of the system 100 may occur remotely, for example, where components of system 100 may be spread across one or more devices of a distributed network. In other examples, interfacing between components of the system 100 may occur locally, for example, where components of system 100 may be located in the same device.

Sensor 102 may be configured to detect data related to biochemical parameters of one or more areas of the human body. In aspects, sensor 102 may be a wireless biocompatible sensor device (biosensor). Sensor 102 may be a multi-layer, biochemically-sensitive device or structure that is operable to be implanted next to, or within, a breast biopsy cavity or cancer tumor percutaneously or in a minimally invasive manner. A non-exhaustive list of example sensors include, quantum dots, metal nanoparticles, carbon nanotubes, silica nanoparticles, nanoshells, gold nanometer cantilevers, and biological microelectromechanical systems (bioMEMS), nanorods, composite material structures filled with chemically sensitive contrast agents, NMR/MRI responsive agents with on board circuits that help discern changes in contrast or material. In examples, sensor 102 may be a size that facilitates being implanted in a minimally invasive manner. For instance, sensor 102 may be sized on the scale of nanometers or centimeters such that sensor 102 may be implanted percutaneously, and may be anchored to a particular location in a biopsy cavity. In a particular example, sensor 102 may be sized between 200 nm and 2 cm in length.

In some aspects, sensor 102 may be, comprise, or be coupled to a site marker. As described above, the composition and shape of a site marker may enable the site marker and/or sensor 102 to be visualized in a variety of external imaging modalities. Similar to the site marker, sensor 102 may comprise, or be comprised of, various components of various characteristics (e.g., densities, chemistries, etc.). In examples, these characteristics may provide for several benefits. For example, such characteristics may provide for enhancing the placement of sensor 102 within a biopsy cavity such that the placement prevents unintentional or arbitrary displacement of the sensor; enhancing the visualization and localization of the sensor through external imaging modalities or other methods; optimizing the sensitivity and specificity of the sensor to capture, bind and/or target specific biomarkers; and enhancing the ability of the sensor to illuminate (and the depth at which the illuminated sensor may be detected) in the biopsy cavity tissue. As another example, such characteristics may provide for enhancing the biocompatibility of the sensor and reducing the foreign body response (tissue inflammatory response) to the sensor to avoid excessive scar/capsule formation that could limit the sensor's sensitivity and long term functionality. For instance, sensor 102 may be coated with one or more anti-inflammatory layers to prevent protein attachments to the sensor. Coatings that are oxygen-permeable, enzyme-based, or made using polymer conjugations for implants comprising natural, synthetic, and semi synthetic materials (e.g. alginate, chitosan, collagen, dextra, hyluronan, polyvinyl alcohol (PVA), polylactic acid (PLA), poly lactic-co-glycolic acid (PLGA), polyethylene glycol (PEG), polyurethanes, combination thereof) may be used to reduce biofouling/tissue response between the tissue and sensor surface(s). In such an example, the foreign body response may be reduced by manipulating one or more properties of sensor 102, such as shape, size, surface area, surface chemistry, roughness, morphology, porosity, composition, sterility, contact duration and degradation.

In aspects, sensor 102 may comprise, or be comprised of, one or more materials. For example, sensor 102 may be soft and flexible, rigid, or some combination thereof. In some aspects, sensor 102 may comprise one or more sections and/or components. For instance, sensor 102 may include an external case that serves as tissue/sensor interface. The external case may be composed of one or more membranes and/or coatings permeable to specific biomarkers or molecules ($O_2$). In some examples, the external case may be loaded with one or more antibodies for the specific binding of biomarkers (such as covalent bonding between antibody/ligand and target to enhance strongest bond). In such an example, polymer coatings (such as PEG, dextran, etc.) may bind to a specific target, and produce a measurable signal characteristic for a property of that target. In other examples, the external case may be loaded with, for example, a nuclear magnetic resonance (NMR) sensor with chemically active contrast agents, a dye within the near-infrared (NIR) excitation and emission spectra, an electrical coil (for mutual inductance), a complimentary metal-oxide-semiconductor integrated circuit (CMOS IC) for radio frequency detection, a hydrogel scaffold that contains fluorescent chemical that detects specific biomarkers, or some combination thereof.

In some aspects, sensor 102 may comprise a drug dispensing mechanism and/or drug eluting mechanism (not illustrated). For example, sensor 102 may comprise a drug delivery system comprising at least a drug reservoir, an oxygen sensor, and a catheter. The drug delivery system may be implemented as a closed feedback loop such that, upon detecting changes to the oxygen levels in a microenvironment, the drug delivery system may release one or more drugs into the microenvironment. In examples, the drug delivery system may be operable to perform high throughput in vivo drug sensitivity testing. In such examples, the drug delivery system may comprise a variety of chemotherapy drugs that are directly released in microdoses to a neoplastic environment in order to evaluate and/or predict drug sensitivity and efficacy in defined regions of exposure. This approach is an improvement over conventional approaches that systemically administer the drugs, which requires a longer period of time. In some aspects, sensor 102 may comprise an oxygen generation and/or dispersal mechanism. For example, sensor 102 may comprise an ultrasound receiver, such as micro-oxygen generator. Upon receiving an ultrasonic trigger from an external device, such as surveillance system 104, the ultrasound receiver may cause the oxygenation of an in situ tumor or microenvironment using water electrolysis. Although specific implementations of sensor 102 are listed herein, one skilled in the art will appreciate that sensor 102 may comprise, or be comprised of, more or fewer materials, sections and/or components within the scope of the technology.

In aspects, the site marker may be operable to mark a potential cancerous lesion within the human body. For example, the site marker may serve to identify the location of the cancerous lesion within a patient's breast in order to perform subsequent image scans on the patient. The site marker may be visually identifiable on an image obtained using an imaging modality, such as radiography, MM, ultrasound, tomography, etc. In some aspects, sensor 102 may be operable to detect data related to biochemical parameters of the implant site. For example, sensor 102 may comprise circuitry for monitoring the implant site and the surrounding areas of the implant site for traces of biochemical parameters. The monitoring may include determining the presence (or absence) of specific enzymes or antibodies using a physiochemical detector. As a particular example, the monitoring may comprise the use of a multilayer composition that includes layers of surface detection using one or more antibodies that bind with specific biomarkers/proteins.

Upon detection of one or more biochemical parameters (or an associated biological response), sensor 102 may collect and timestamp the biochemical parameter data. The biochemical parameter data may then be provided to (or made accessible to) a surveillance system. For example, sensor 102 may store the biochemical parameter data in a local data store. Alternately or additionally, sensor 102 may convert the biochemical parameter data into a set of electrical signals using, for example, a transducer and corresponding circuitry. The electrical signals may be provided to a surveillance system. In such examples, the monitoring may occur in real-time, periodically, on-demand or in response to the satisfaction of one or more criteria. In other aspects, sensor 102 may not be operable to directly detect and/or collect data related to biochemical parameters of the implant site. For example, sensor 102 may not comprise monitoring/detection circuitry. Instead, sensor 102 may be a device having a structure that is modifiable based on the conditions of the implant site or external stimuli. In such an example, a surveillance system may beam electromagnetic waves to (or through) the structure. Alternately, the surveillance system may emit a known excitation wavelength, such as an NIR wavelength, that may excite the structure. The use of NIR wavelengths may enable deep penetration (e.g., approximately two or more centimeters) through heterogeneous tissue, and provide increased absorption band (e.g., approximately 650-900 nm). Moreover, the NIR wavelengths may provide for a high signal-to-noise ratio and a low scattering loss. The excited structure may fluoresce or emit a signal proportional to the presence of a specific biomarker captured by, measured by, or binded to sensor 102. The surveillance system may measure, collect and/or process data associated with the electromagnetic waves or the fluorescence emission emitted by the sensor to enable the dynamic, continuous monitoring of the presence of biomarkers within the microenvironment.

In aspects, sensor 102 may be internally or externally powered. For example, sensor 102 may comprise an internal power source. The internal power source may be in an always-on state, or may be activated in accordance with one or more of the monitoring options discussed above. In another example, sensor 102 may be activated externally and/or powered externally via one or more wireless power transfer techniques, such as non-radiative (near-field) power transfer and radiative (far-field) power transfer. Non-radiative power transfer, as used herein, may refer to the transfer of power by magnetic fields (using inductive coupling between coils of wire) or by electric fields (using capacitive coupling between metal electrodes). Radiative power transfer, as used herein, may refer to the transfer of power by beams of electromagnetic radiation (such as microwaves, laser beams, or infrared) or by wireless ultrasonic power.

Surveillance system 104 may be configured to receive biochemical parameter data from sensor 102. In examples, surveillance system 104 may be, or may be implemented in, one or more devices. For instance, surveillance system 104 may be implemented in a mobile phone, a wearable device, a tablet, a laptop computer, or the like. Alternately, one or more features of surveillance system 104 may be distributed across one or more such devices. In aspects, surveillance system 104 may have access to sensor 102 and information stored thereon. Surveillance system 104 may receive or collect biochemical parameter data from sensor 102 in real-time, periodically, on-demand or in response to the satisfaction of one or more criteria. The received/collected biochemical parameter data may be processed and/or stored in a data store accessible to surveillance system 104. In examples, processing the biochemical parameter data may include parsing the data according to one or more criteria and evaluating the parsed data to identify one or more trends. The raw biochemical parameter data and/or the evaluated biochemical parameter data may then be displayed on a display area of surveillance system 104. In some aspects, surveillance system 104 may transmit (or otherwise make available) the biochemical parameter data to an external input processing system, such as processing unit 106.

Surveillance system 104 may be further configured to transmit biochemical parameter data to sensor 102. In aspects, surveillance system 104 may have access to a set of biochemical parameters. Surveillance system 104 may select, or receive a selection of, one or more parameters from the set of biochemical parameters. The selected biochemical parameters may represent the parameters to be monitored by sensor 102. In examples, biochemical parameters may be selected based on a prescribed treatment, a reaction to a treatment, or a manual selection. The selection of biochemical parameters may then be transmitted to, and implemented by, sensor 102.

Input processing system 106 may be configured to process biochemical parameter data. In aspects, input processing system 106 may have access to data collected and/or generated by sensor 102 and/or surveillance system 104. Input processing system 106 may analyze the data to detect trends in the implant site, monitor the progress of a treatment, or adjust a treatment to tailor a personalized treatment. Alternately, input processing system 106 may provide no, minimal, or partial analysis functionality. In such examples, input processing system 106 may provide data collected by sensor 102 and/or surveillance system 104 to a separate processing system, service or environment. For instance, input processing system 106 may provide collected data to distributed network environment (not illustrated), such as a cloud-based environment. The distributed network environment may be leveraged to analyze vast amounts of patient data incorporating, for example, demographic information (e.g., age, gender, education, residence information, income, occupation, etc.), behavioral information (e.g., appointment history, prescription events, health-related events/patterns, etc.), psychographic information (e.g., values, interests, opinions, attitudes, personality, etc.), risk factors, family history, breast density, genetic carrier (BRCA1, BRCA2), tumor receptor carrier (ER, HER2, etc), etc. The analyzed patient data may be compared to similar patient data, previously received patient data, theoretical data sets, etc. Alternately, the analyzed (and/or unanalyzed) patient data may be evaluated using one or more statistical, predictive or diagnostic models or algorithms. For instance, a set of patient data may be provided as input to a diagnostic model implemented on, or accessible by, a distributed network environment. In examples, the diagnostic model may be trained using labeled and/or unlabeled data sets of simulated and/or real patient data. As a result of the training, the diagnostic model may be able to determine one or more treatment practices for a patient or patient population. In at least one example, the diagnostic model may be operable to rank the treatment practices according to a set of criteria to determine the optimal or most effective treatment practice for a patient or patient population. The ranking may include using aspects of the patient data to generate a set of scores or confidence metrics for the treatment practices, and ordering the treatment practices based on the scores/metrics.

In aspects, the analyzed data and/or treatment practices may be presented on a user interface, and/or manipulated using a corresponding application or set of instructions. For example, a multidisciplinary team of physicians may have access to analyzed biochemical parameter data. At least one of the physicians may compare the biochemical parameter data to previously-collected biochemical parameter data to monitor the progress of neoadjuvant or adjuvant chemotherapies for a patient. Based on the comparison, the physician may be able to determine the effectiveness of a treatment in real-time, or in a time period considerably less than that afforded by using external imaging modalities. The physician may then adjust the treatment or tailor treatment accordingly. In another example, a treatment practice may be presented to one or more physicians via the user interface. The user interface may comprise medical information related to individual treatment practices, such as prescribed medications and associated information (e.g., recommended dosages, medication schedules, suppliers, etc.), relevant medical facilities, useful resources (e.g., websites, medical journals/articles, studies, FAQs, contact information for other medical professionals/specialists, etc.), treatment roadmaps, etc. Alternately, the user interface may comprise one or more actionable controls or elements enabling the actuation of one or more of the treatment practices, or events associated therewith. For example, sensor 102 may comprise a bidirectional radio circuit. The user interface may provide controls/elements that enable a user to provide a set of instructions to sensor 102 via the bidirectional radio circuit. In response to receiving the set of instructions, sensor 102 may perform one or more actions as specified by the set of instructions.

Figure 2A:
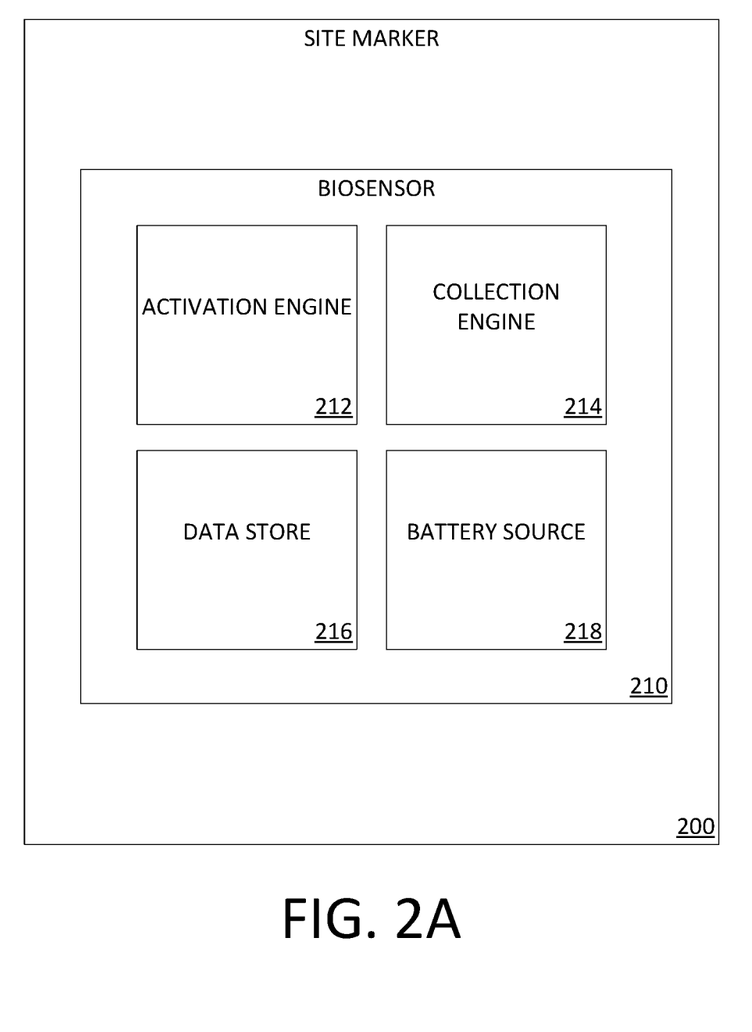
FIG. 2A illustrates a diagram of a wireless biocompatible sensor as described herein.
Figure 2B:
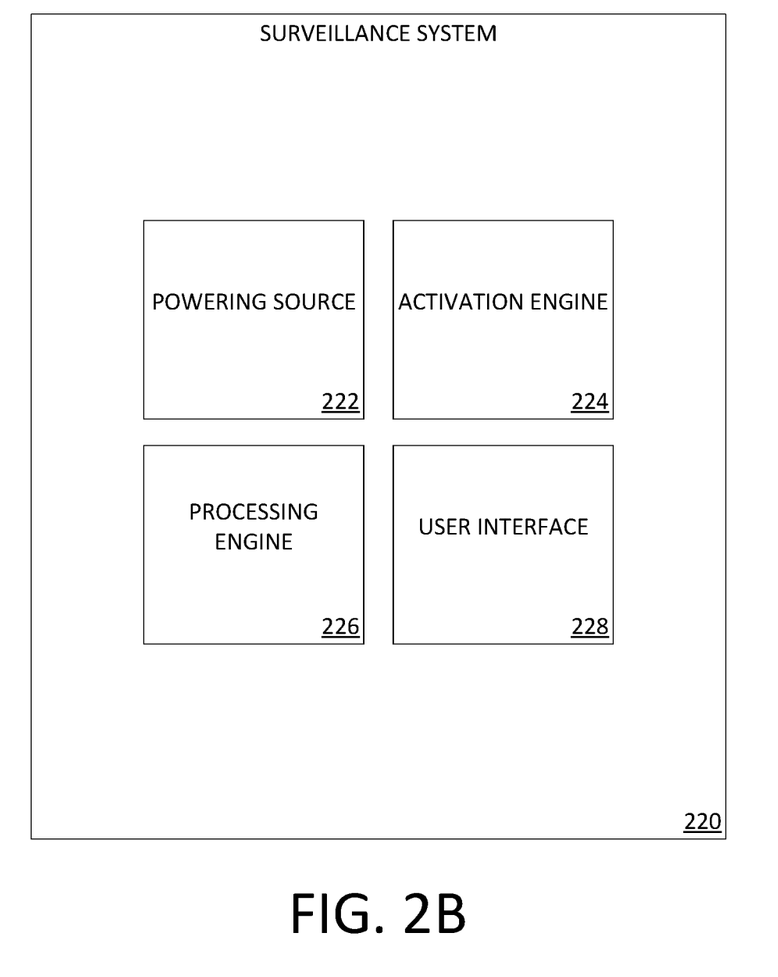
FIG. 2B illustrates a diagram of a surveillance system for monitoring the wireless biocompatible sensor of FIG. 2A as described herein.

FIGS. 2A and 2B illustrate diagrams of a biosensor 210 and surveillance system 220, respectively, for the active monitoring of a wireless biosensor, as described herein. The active monitoring techniques implemented by biosensor 210 and surveillance system 220 may comprise the active monitoring techniques and content described in FIG. 1. In alternative examples, a single system (comprising one or more components such as processor and/or memory) may perform the processing described in systems 210 and 220, respectively.

With respect to FIG. 2A, site marker 200 may comprise biosensor 210. Site marker 200 may be permanent (or long-term), composed of a biocompatible material and configured to mark a site of interest within a biological organism. In examples, site marker 200 may be identifiable using one or more imaging modalities, such as radiography, MRI, ultrasound, tomography, etc. Biosensor 210, in turn, may comprise activation engine 212, collection engine 214, data store 216 and battery source 218. Activation engine 212 may be configured to activate biosensor 210. In aspects, activation engine 212 may receive an activation signal from biosensor 210 or an external device, such as surveillance system 220. The activation signal may cause biosensor 210 (or the data collection/transport functionality thereof) to resume or initiate from a suspended or off state. For instance, upon receiving an activation signal, activation engine 212 may activate collection engine 214. In examples, the activation signal may be received in accordance with a periodic schedule, an on-demand request, or in response to the satisfaction of one or more criteria. Activation engine 212 may be further configured to update a set of biochemical parameters. In aspects, an activation signal received by activation engine 212 may comprise a set of biochemical parameters. Activation engine 212 may use the set of biochemical parameters to set or update a preexisting set of biochemical parameters. For example, data store 216 may store a first set of biochemical parameters for which data is collected by biosensor 210. When a second set of biochemical parameters is received, activation engine 212 may update the first set of biochemical parameters accordingly.

Collection engine 214 may be configured to collect biochemical data from a biological organism. In aspects, collection engine 214 may identify a set of biochemical parameters. Identifying a set of biochemical parameters may comprise evaluating configuration settings, a biochemical profile, a stored set of biochemical parameters, or the like. For example, collection engine 214 may identify a biochemical profile for a patient. The biochemical profile may be stored by biosensor 210 or received from an external service or device. The biochemical profile may specify a set of biochemical parameters to be monitored for the patient during the next data collection cycle. Collection engine 214 may then use monitoring circuitry to monitor the implant site and surrounding areas for traces of the identified biochemical parameters. Upon detection of the monitored biochemical parameters, collection engine 214 may collect data for one or more of the monitored biochemical parameters. In some examples, the collected data may be stored in data store 216 and/or transmitted to an external service or device. Transmitting the collected may include converting the biochemical parameter data into a set of electrical signals and providing the set of electrical signals to an external service or device. In other examples, the collected data may not be transmitted to an external service or device. Instead, an indication of the collected data may be transmitted. For instance, a completion indicator (e.g., a flag, pointer, success code, etc.) may be generated after the successful completion of a data collection cycle. The completion indicator may be correlated or assigned to the set of data generated during the data collection cycle. Collection engine 214 may transmit the completion indicator to an external service or device. The external service or device may subsequently use the completion indicator to access the corresponding set of data.

Battery source 218 may be configured to provide power to site marker 200 and/or biosensor 210. In some aspects, battery source 218 may be powered by an internal power source. The internal power source may be in an always-on state, or may be activated in accordance with one or more conditions. In other aspects, battery source 218 may powered by be an external power source via one or more wireless power transfer techniques. Such wireless power transfer techniques may include inductive coupling, resonant inductive coupling, capacitive coupling, magnetodynamic coupling, microwaves, light waves, etc. In at least one aspect, site marker 200 and/or biosensor 210 may be made of, or comprise, piezoelectric material. In such an aspect, battery source 218 may be externally powered using, for example, ultrasound waves and piezoelectricity.

With respect to FIG. 2B, surveillance system 220 may represent a service or device external to site marker 200 and/or biosensor 210. Surveillance system 220 may comprise powering source 222, activation engine 224, data processing engine 226 and user interface 228. Powering source 222 may be configured to provide power to biosensor 210. In aspects, powering source 222 may externally power biosensor 210 using one or more wireless power transfer techniques, as described with respect to battery source 218. Powering source 222 may provide wireless power transfer techniques in accordance with one or more conditions. For example, powering source 222 may provide power to biosensor 210 prior to providing data to, or requesting data from, biosensor 210. Alternately, powering source 222 may provide power to biosensor 210 at set intervals (e.g., once an hour, twice a day, etc.). Activation engine 224 may be configured to send an activation signal to biosensor 210. In aspects, activation engine 224 may generate an activation signal used to activate biosensor 210. The activation signal may cause collection engine 214 to initiate the collection of biochemical data from a biological organism. In examples, the activation signal may comprise (or be accompanied by) a set of instructions. The set of instructions may provide for altering the state of biosensor 210, retrieving data from biosensor 210 and/or providing data to biosensor 210. For instance, activation engine 224 may generate an activation signal comprising a set of biochemical parameters. The set of biochemical parameter may specify one or more biochemical parameters to be monitored by biosensor 210. In aspects, activation engine 224 may transmit the activation signal (and/or an accompanying set of instruction) to biosensor 210.

Data processing engine 226 may be configured to process data received from biosensor 210. In aspects, data processing engine 226 may have access to data collected by biosensor 210 and/or data collected from other data sources. For example, data processing engine 226 may have access to data located on, or generated by, one or more additional sensors, surveillance systems, imaging systems, other data processing systems, or users. The data may comprise current and/or historical biochemical parameter data, patient data, imaging scans or user input. As one example, data processing engine 226 may have access to a data store comprising ultrasound or MM data measuring the periodic changes in the size and/or compositions, signal enhancement of a tumor during neo adjuvant chemotherapy. As another example, data processing engine 226 may have access to a user interface, such as user interface 228. The user interface may provide processing engine 226 access to user input relating to a patient or treatment practice. For instance, the user interface may enable a user (e.g., a physician, physician assistant, etc.) to enter size information for a tumor (e.g., diameter, length, echogenicity, margins, signal enhancement, phenotype, lesion distribution focal or multifocal, etc.) as measured by ultrasound at the time the sensor is implemented, or by using the MM image. This entered input may then serve as the baseline anatomical reference of the tumor. In aspects, the data accessible to processing engine 226 may comprise microenvironment biochemical data and/or macroenvironment anatomical data. The use of microenvironmental data and macroenvironmental enables data processing engine 226 to evaluate noninvasive (or minimally invasive) monitoring data with noninvasive imaging data.

Upon accessing the data, data processing engine 226 may perform one or more processing steps. In examples, the processing may include parsing the data to identify, for example, biochemical parameter data, and organizing the parsed data according to a set of criteria. In some examples, the processing may further include evaluating the parsed data to identify one or more trends in the implant site to drive to a desired prognosis for a pathologic complete response, identify trends in a patient population, monitor the progress of a treatment, adjust a treatment to tailor a personalized treatment, provide a notification or warning, generate a textual or graphical report, etc. In such examples, the evaluation may comprise the use of one or more rule sets, algorithms or models. A model, as used herein, may refer to a statistical, predictive or diagnostic model that may be used to correlate biochemical parameters or biomarkers with trends or treatment responses in a specific microenvironment (such as a neoplastic environment, a tumor or biopsy site). Such a model may be a rule-based model, a machine-learned regressor, a machine-learned classifier, or the like. In aspects, data processing engine 226 may transmit the processed biochemical parameter data and/or unprocessed biochemical parameter data to one or more external processing systems, such as input processing system 106. Alternately, data processing engine 226 may present some portion of the processed and/or unprocessed biochemical parameter data using a display component, such as user interface 228. User interface 228 may be configured to enable navigation of, or interaction with, the processed biochemical parameter data and/or one or more treatment practices. As described above, enabling users/patients to view the biochemical parameter data (and changed thereto) in real-time may ease patient's stress, anxiety, depression, and economic cost. In some aspects, user interface 228 may provide access to a set of configuration settings. The configuration settings may enable a user to specify biochemical parameters to monitor, power states and settings, monitoring schedules or events, presentation options, and the like.

Having described various systems that may be employed by the aspects disclosed herein, this disclosure will now describe one or more methods that may be performed by various aspects of the disclosure. In aspects, methods 300 and 400 may be executed by an example system, such as system 100 of FIG. 1 or the site marker 200 of FIG. 2. In examples, methods 300 and 400 may be executed on a device comprising at least one processor configured to store and execute operations, programs or instructions. However, methods 300 and 400 are not limited to such examples. In other examples, methods 300 and 400 may be performed on an application or service for performing active monitoring of a wireless biosensor. In at least one example, methods 300 and 400 may be executed (e.g., computer-implemented operations) by one or more components of a distributed network, such as a web service/distributed network service (e.g. cloud service).

Figure 3:
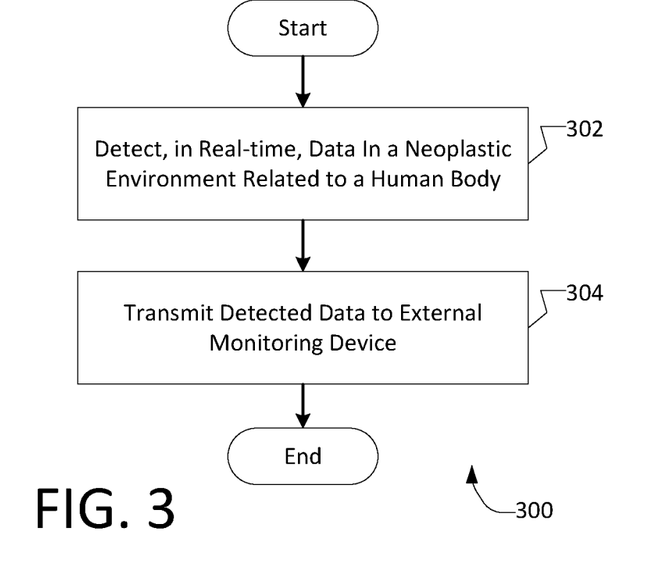
FIG. 3 illustrates an example method for detecting biochemical parameter data using a wireless biocompatible sensor as described herein.

FIG. 3 illustrates an example method 300 for detecting biochemical parameter data using a wireless biosensor, as described herein. Example method 300 begins at operation 302, where a biosensor may detect data related to a biological organism. In aspects, a site marker, such as site marker 200, may be implanted next to, or within, a site of interest in a biological organism. The site marker may mark the implant area such that the implant area may be identifiable using one or more imaging modalities. The site marker may comprise or be coupled to a wireless biocompatible sensor device (biosensor), such as biosensor 210. The biosensor may be operable to receive a one or more activation signals from a device, such as a site marker or an external surveillance system. In examples, the activation signal may comprise (or be accompanied by) a set of instructions for altering the state of the biosensor, retrieving data from the biosensor and/or providing data to the biosensor. In response to receiving such a signal, the biosensor may initiate the real-time monitoring of the implant site and surrounding areas of the biological organism for traces of biochemical parameters. For example, a site marker comprising a biosensor may be implanted in a breast biopsy cavity percutaneously or in a minimally invasive manner.

In aspects, the biosensor may be configured to collect data in real-time for biochemical parameters that are known or suspected to be linked to a breast cancer tumor's microenvironment. Such biochemical parameters may include circulating tumor cells, circulating tumor DNA, proteins, serum soluble human epidermal growth factor receptor 2 (HER2)/neu oncogene, urokinase plasminogen activator (UPA) and plasminogen activator inhibitor-1 (PAI-1) biomarkers, oxygen levels; pH levels; nitric oxide and interstitial fluid pressure. For example, the biosensor may be configured to collect biochemical parameter data for the following operational ranges:

circulating tumor DNA>1 cell in 7.5 ml of blood;
circulating tumor DNA cell percentage (or cell count) from 0 to 100%;
urokinase plasminogen activator (UPA) and plasminogen activator inhibitor-1
(PAI-1) from 0 to 100 ng/mg;
pH levels from −7 to +7;
oxygen levels: ranges from 0.01 mm Hg to 100 mm Hg;
interstitial fluid pressure from −1 to +50 mm Hg
nitric oxide: 0 to 100%;
lactate and ATP: 0 to 100%

Upon receiving an activation signal from an external surveillance device, such as surveillance system 220, the biosensor may initiate monitoring the breast biopsy cavity for the presence (or absence) of specific enzymes or antibodies related to a biological organism in which the biosensor is implanted. In examples, the monitoring period may be predefined, specified in local configuration setting or specified in the activation signal. Upon detecting one or more biochemical parameters (or an associated biological response), the biosensor may collect and timestamp the detected biochemical parameter data. The detection may comprise determining whether the biochemical parameter data is within a certain range of values or whether a set of criteria has been satisfied. In one example, the determination may comprise comparing biochemical parameter data with one or more thresholds, or evaluating the biochemical parameter data against a rule set or decision logic.

At operation 304, collected data may be transmitted to an external monitoring device. In aspects, the biosensor may store the collected biochemical parameter data in a storage location, such as data store 216. Alternately or additionally, the biosensor may transmit the collected biochemical parameter data to an external surveillance device. Transmitting the collected biochemical parameter data may include timestamping the data and/or inserting one or more annotations into the data. Transmitting the biochemical parameter data may also include converting the data into a set of electrical signals and providing the set of electrical signals to the external surveillance device. For instance, the biosensor may emit fluorescent emissions to convey the presence (or absence) of one or more biomarkers. The external surveillance device may convert the fluorescent emissions to a set of electrical signals and interpret the set of electrical signals. Alternately, the biosensor may convert the fluorescent emissions to a set of electrical signals and transmit the set of electrical signals to the external surveillance device.

Figure 4:
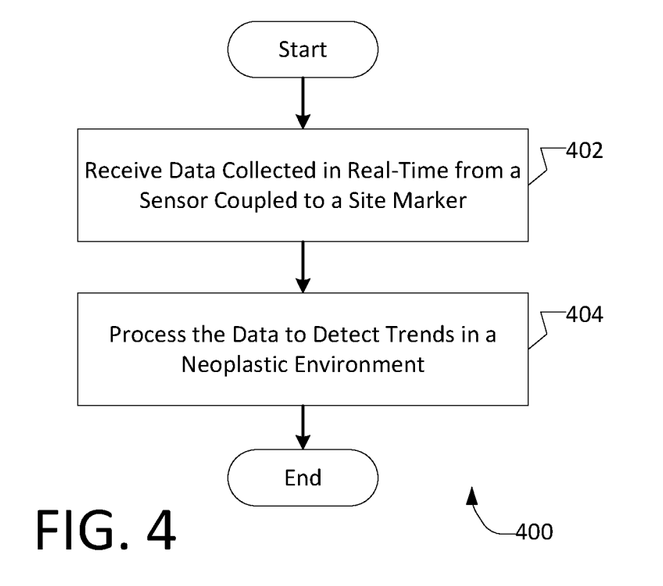
FIG. 4 illustrates an example method for collecting biochemical parameter data from a wireless biocompatible sensor as described herein.

FIG. 4 illustrates an example method 400 for collecting biochemical parameter data from a wireless biosensor, as described herein. Example method 400 begins at operation 402, where data related to a biological organism is collected from a biosensor. In aspects, a monitoring system, such as surveillance system 220, may have access to biochemical parameter data collected by a biosensor, such as biosensor 210. In some examples, the access may enable the monitoring system to passively collect the data. For instance, the biosensor may initiate the transmission of the data, and the monitoring system may simply receive the transmitted data. In other examples, the access may enable the monitoring system to actively collect the data. For instance, the monitoring system may initiate a data retrieval process to retrieve the data from the biosensor or a storage location comprising the data, such as data store 216. In yet other examples, a monitoring system may collect data in the form of user input. For instance, a user interface may be used to enter user input comprising biochemical parameter data relating to a patient or treatment practice. In a specific example, the user input may correspond to measurements representing a baseline anatomical reference for a tumor.

At operation 404, collected data may be processed to determine one or more trends. In aspects, a data processing component, such as data processing engine 226 may have access to data received from a biosensor. Upon accessing the data, data processing component may perform one or more processing steps. The processing may include parsing the data, and organizing the parsed data according to a set of criteria. For instance, a parsing operation may be applied to the data to identify biochemical parameters and associated data. The biochemical parameter data may then be organized, for example, chronologically by individual biochemical parameters, alphanumerically by biochemical parameter name/label, according the determined or perceived importance/relevance of biochemical parameters, or according to the most atypical or out-of-range biochemical parameters values. The processing may further include using the biochemical parameter data to generate one or more feature vectors. A feature vector, as used herein, may refer to an n-dimensional vector of numerical features that represent one or more objects. Generating a feature vector may include identifying one or more features in the biochemical parameter data, calculating feature scores for the identified features, and adding the features and the corresponding feature scores to a feature vector. In at least one aspect, calculating the feature scores may include applying weights or multipliers to one or more biochemical parameters to reflect the importance/relevance of biochemical parameters. For instance, a biochemical parameter may be identified as highly indicative of a disease/condition. As a result, the data processing component may apply a multiplier, such as ×2.0, to a biochemical parameter value or corresponding feature score. Alternately, the relative importance of one or more biochemical parameters may be determined with respect to the entire set of biochemical parameters. For instance, a large amount of biochemical parameters having slightly elevated weights/multipliers (representative of biochemical parameters that are slightly indicative of a disease/condition) may be collectively viewed as more important/relevant that a single biochemical parameter (or a small amount of biochemical parameters) having greatly elevated weights/multipliers.

In some aspects processing the collected data may comprise matching and evaluating biochemical parameter data against user input and/or data generated by one or more imaging modalities. For example, the user-provided, anatomical measurements for a tumor may be verified or evaluated against biochemical parameter data collected from a biosensor and/or images generated using one or more imaging modalities. Such a matching/evaluation of noninvasive (or minimally invasive) monitoring techniques may provide for using biochemical parameter feature scores to verify the progress or effectiveness of a treatment. For instance, a first set of biochemical parameter data may correspond to a first set of, for example, ultrasound images of a tumor. After one or more treatments have been applied to the tumor, a second set of biochemical parameter data and a second set of corresponding ultrasound images of a tumor may be generated/collected. The first and second set of ultrasound images may indicate that the size of the tumor has decreased. The first and second set of biochemical parameter data may then be evaluated/compared to identify changes in the biochemical parameters, and to determine correlations between changes in the biochemical parameters and changes in the size/dimensions of the tumor. In at least one example, the biochemical parameters that have changed may further be evaluated using one or more algorithms/models to determine weights/scores representing the relevance of the biochemical parameters (or sets/combinations of biochemical parameters) to the changes in the tumor. For instance, the detected increase in circulating tumor cells and the decrease in oxygen in a microenvironment may result in the assignment of large weights/scores to the corresponding individual biochemical parameters. However, the circulating tumor cells and oxygen level biochemical parameters as a set (e.g., a two-parameter subset) may be assigned an even larger weight/score than the weights/scores assigned to the individual biochemical parameters. This increase in the assigned weight/score may reflect that the two-parameter subset is more relevant to the changes in the tumor than either of the biochemical parameters individually.

In some aspects, the processing may further include evaluating the parsed data to identify one or more trends in the implant site. As an example, the parsed data, raw biochemical parameters data and/or feature vectors may be provided as input to a diagnostic model or diagnostic modelling utility. The diagnostic model may be used to determine one or more trends for the biosensor implant site, and/or determine correlations between the trends and a microenvironment's response to treatment. For instance, the diagnostic model may be used to determine that the following correlations between biochemical parameters and one or more conditions/diseases, such as breast cancer:

Increased circulating tumor cells or circulating tumor DNA is indicative of an advanced cancer stage and/or tumor aggressiveness;

Increased circulating protein (serum HER2/neu or estrogen receptor ER) is indicative of correlated to larger tumor size and faster development;

Increased UPA and PAI-1 induces poor outcomes (for example, <3 ng/mg of protein for UPA is indicative of cancer invasiveness, whereas <14 ng/mg of protein for PAI-1 is indicative of enhanced cancer progression and angiogenesis;

Decreased oxygen in a microenvironment affects gene expression and protein biosynthesis, increases cancer cell survival, and is indicative of aggressive metastatic spread (for example, <45 mmHg of oxygen in the blood indicates that a tumor is hypoxic);

Decreased pH in a microenvironment is indicative of tumor aggressiveness and metastatic influence (for example, low oxygen levels causes tumor cells to produce glycolysis, accumulate lactate, and push protons to extracellular space);

Increased nitric oxide affects chemotherapy resistance, metastasis and angiogenesis, and is indicative of tumor progression and advanced cancer stages;

Increased interstitial fluid pressure is indicative of solid tumors and potentially reduced chemotherapy delivery (for example, solid tumors have reduced blood flow, which may affect the delivery of chemotherapy agents to the site).

As a specific example, a diagnostic model may identify consistently elevating levels of circulating tumor cells in an implant site microenvironment. The diagnostic model may analyze the identified data using one or more data sources or utilities, such as a repository of previously-collected data and outcomes, an image classifier, a predictive model, a human subject matter expert, etc. Based on the analyzed data or specific biomarkers, the diagnostic model may correlate elevated levels of circulating tumor cells to an advanced stage of cancer and/or tumor aggressiveness. In such an example, the output form the diagnostic model may be used to determine a treatment or assess a microenvironment's response to treatment.

In some aspects, the data processing component may make the processed data and/or biochemical parameters data accessible to a user and/or external system. For example, the processed data may be presented using a display interface accessible to the monitoring system, such as user interface 228. The display interface may provide for interacting the processed (and/or raw) biochemical parameter data, interacting with the biosensor, managing monitoring periods, modifying biochemical parameters to monitor, generating warnings/alarms, transmitting data to remote services/devices, viewing/setting configuration settings for the monitoring system, etc. As another example, the data processing component may provide the processed data and/or biochemical parameter data to a data analysis platform, such as input processing system 106. The data analysis platform may perform one or more of the data processing steps described above with respect to the data processing component (e.g., trend detection, treatment monitoring, treatment tailoring/personalization, etc.). Additionally, the data analysis platform may provide for anonymizing and/or storing the data and/or biochemical parameter data. The anonymized/stored data may subsequently be compared to a user profile or data profile to determine or evaluate one or more trends. For instance, a set of processed patient data may be compared to a data profile comprising data for an anonymized patient population. Based on the comparison, one or more trends or treatment options may be determined.

In some aspects, the data analysis platform may be installed in (or otherwise accessible by) one or more health care facilities. A multidisciplinary team of physicians may have access to the data analysis platform from one or more of the health care facilities. The data analysis platform may comprise a display interface having the functionality described above. In aspects, the display interface may generate and/or present treatment-related information, such as warnings, notifications, reports and/or action items. For example, the data analysis platform may determine the data collected for one or more biochemical parameters exceeds permissible bounds. As a result, the data analysis platform may generate and transmit an alert to multiple devices, such as the patient's monitoring system, a physician's mobile device, a set of health care facility devices, etc. In response, one or more of the devices receiving the alert may automatically generate a "Schedule Appointment" action item for the patient.

In aspects, the team of physicians may individually or collaboratively evaluate biochemical parameter data for one or more patients. Such evaluation may include comparing the biochemical parameter data to previously-collected biochemical parameter data to monitor a microenvironment of interest, or the progress of neoadjuvant or adjuvant chemotherapies. In at least one example, the previously-collected biochemical parameter data may correspond to baseline biochemical measurements. The baseline biochemical measurements may be recorded for one or more aspects of a microenvironment at the time a biosensor is implanted. Biochemical parameter data subsequently collected for the microenvironment may be compared to the baseline biochemical measurements (and/or other previously-collected biochemical parameter data) to monitor the microenvironment and/or to evaluate the effectiveness of one or more courses of action. In some aspects, based on the comparison of biochemical parameter data, one or more of the physicians may be able to determine the effectiveness of a treatment in real-time, or in a time period abbreviated from the time period afforded by using external imaging modalities. The team of physicians may then evaluate treatment options and/or adjust the treatment accordingly.

In examples, effective treatment modifications based on the ability of multidisciplinary physicians to assess and visualize biochemical parameter trends may result in a reduction of ineffective systemic chemotherapy treatments. Such a reduction may, in turn, reduce the toxicity, side effects, and healthcare costs for patients. Similarly, providing these biochemical parameters to multidisciplinary physicians (e.g., surgeon, radiologist, oncologist, etc.) may also allow the physicians to collaboratively assess treatment efficacy by comparing the biochemical parameters to one or more external images. Such collaboration may enable the physicians to provide a patient with a unified treatment response with consensus; thus, enabling the physicians to consolidate and reduce the number of follow up visits. As a specific example, a lesion may be detected in a patient's breast. In response to detecting the lesion, the lesion may be biopsied and a site marker may be implanted at the biopsy site. The site marker may be, comprise, or be coupled to a biosensor, such as sensor 102. Upon implanting the site marker (and the corresponding biosensor), baseline measurements for one or more biochemical parameter may be recorded using the biosensor. The baseline measurements may indicate, for example, that the amount of circulating tumor cells and serum HER2/neu protein detected in the microenvironment is low, and the amount of oxygen detected in the microenvironment is high. The baseline measurements may be recorded and stored in a data store for future evaluation. After the implant is complete, a surveillance device that may be communicatively coupled to the site marker, such as surveillance system 104, may be provided to the patient, and a follow-up appointment may be scheduled.

Periodically, the site marker/biosensor may detect and transmit biochemical parameter data to the surveillance device in real-time. The surveillance device may evaluate the received biochemical parameter data. Alternately, the surveillance device may transmit the biochemical parameter data to a data processing system, such as input processing system 106, to be evaluated. Evaluating the biochemical parameter data may comprise comparing the received biochemical parameter data with the previously-recorded baseline measurements. In this example, the received biochemical parameter data may indicated the amount of circulating tumor cells and serum HER2/neu protein detected in the microenvironment has increased, and the amount of oxygen detected in the microenvironment has decreased. As a result, the surveillance device may generate a notification or warning indicating the change in the biochemical parameter data. The surveillance device may present the notification/warning to the user via a user interface accessible to the surveillance device, and/or transmit the notification/warning to the patient's physician (or to a data analysis platform accessible by the physician). Based on the notification/warning, an impromptu follow-up appointment may be scheduled for the patient. In this example, the impromptu follow-up appointment may be scheduled for a date that is considerably prior to the original follow-up appointment.

The impromptu follow-up appointment may reveal that one or more lesions have returned. In response, the patient's physician may recommend radiation therapy to treat the lesion(s). Upon deciding to proceed with the radiation therapy treatment, updated baseline biochemical measurements of the lesion microenvironment may be recorded. Over time, as before, the site marker/biosensor may periodically detect and transmit biochemical parameter data to the surveillance device in real-time or by inquiry. In this example, the received biochemical parameter data may indicate that the lesion is not responding to the radiation therapy treatment (e.g., the amount of circulating tumor cells and serum HER2/neu protein detected in the lesion microenvironment has increased or has not decreased appreciably, and the amount of oxygen detected in the microenvironment has decreased or has not increased appreciably). In response, the patient's physician may recommend an alternate dosage of the radiation therapy or an alternate treatment. Upon deciding to proceed with an alternate treatment approach, an updated baseline biochemical measurements of the lesion microenvironment may again be recorded. Over time, the site marker/biosensor may again periodically detect and transmit biochemical parameter data associated with the alternate treatment to the surveillance device in real-time. In this example, the received biochemical parameter data may indicate that the lesion is responding well to the alternate treatment (e.g., the amount of circulating tumor cells and serum HER2/neu protein detected in the lesion microenvironment has decreased or has not further increased, and the amount of oxygen detected in the microenvironment has increased or has not further decreased).

Over the course of several follow-up appointments, biochemical parameter data and/or corresponding images may be evaluated to ensure the lesion is continuing to respond to the treatment. In this example, the biochemical parameter data and/or corresponding images may eventually indicate that the lesion is in remission. This outcome is achieved without the patient having to endure the severe psychological impact (e.g., stress, anxiety, depression, etc.) and protracted waiting periods that are generally entwined with such treatment. Further, the patient is confident that the site marker/biosensor will detect and alert the physician if the lesion (or similar issues in the microenvironment) occur in the future.

Figure 5:
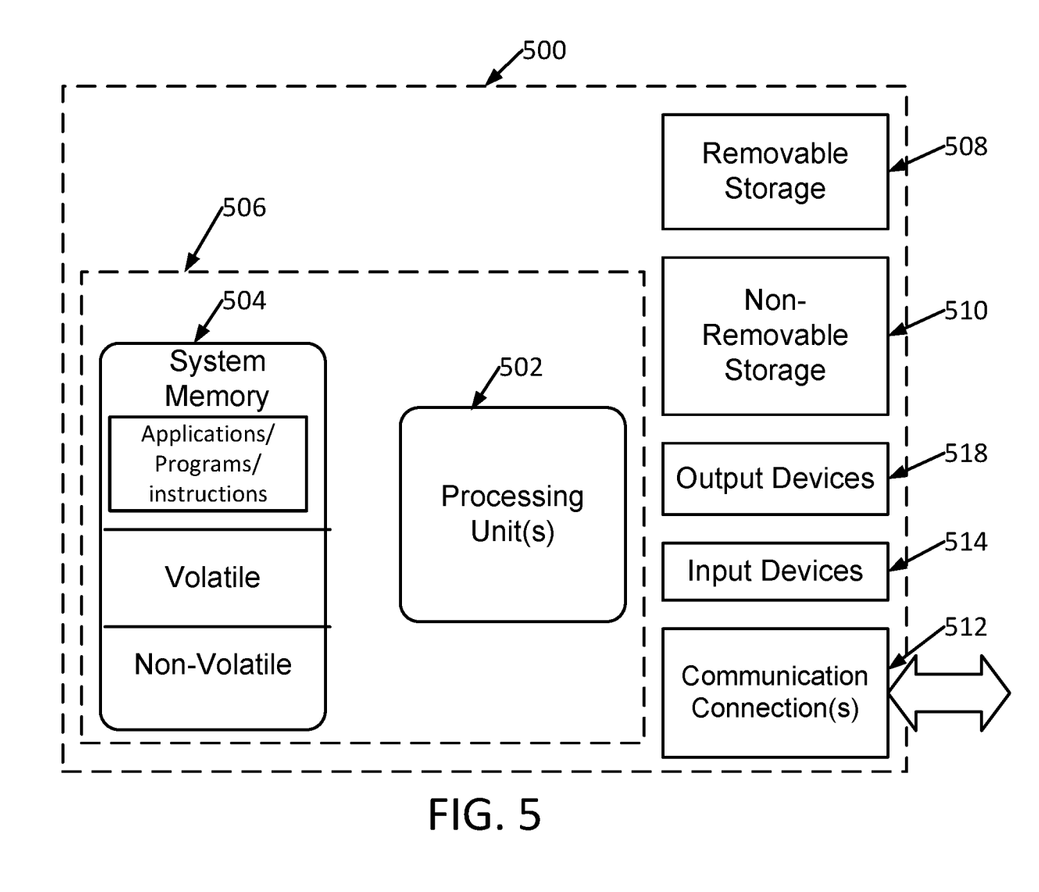
FIG. 5 illustrates one example of a suitable operating environment in which one or more of the present embodiments may be implemented.

FIG. 5 illustrates an exemplary suitable operating environment for detecting biochemical parameter data using a wireless biosensor described in FIG. 1. In its most basic configuration, operating environment 500 typically includes at least one processing unit 502 and memory 504. Depending on the exact configuration and type of computing device, memory 504 (storing, instructions to perform the active monitoring embodiments disclosed herein) may be volatile (such as RAM), non-volatile (such as ROM, flash memory, etc.), or some combination of the two. This most basic configuration is illustrated in FIG. 5 by dashed line 506. Further, environment 500 may also include storage devices (removable, 508, and/or non-removable, 510) including, but not limited to, magnetic or optical disks or tape. Similarly, environment 500 may also have input device(s) 514 such as keyboard, mouse, pen, voice input, etc. and/or output device (s) 516 such as a display, speakers, printer, etc. Also included in the environment may be one or more communication connections 512, such as LAN, WAN, point to point, etc. In embodiments, the connections may be operable to facility point-to-point communications, connection-oriented communications, connectionless communications, etc.

Operating environment 500 typically includes at least some form of computer readable media. Computer readable media can be any available media that can be accessed by processing unit 502 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 500 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method of detecting data related to a human body, the method comprising:
   detecting data related to the human body at a biosensor disposed in a breast cavity in real-time, wherein the data comprises one or more biochemical parameters;
   transmitting the data to an external monitoring device located outside of the breast;
   receiving feedback from the external monitoring device, wherein the feedback relates to the transmitted data and anatomical measurements related to a portion of the breast adjacent the breast cavity, the anatomical measurements comprising at least one of diameter, length, phenotype, and lesion distribution;
   based on the feedback, adjusting a set of biochemical parameters to be monitored; and
   monitoring the adjusted set of biochemical parameters to modify a cancer treatment.

2. The method of claim 1, wherein detecting the data comprises receiving an activation signal from the external monitoring device.

3. The method of claim 2, wherein the activation signal is used to specify a set of biochemical parameters to monitor.

4. The method of claim 1, wherein detecting the data comprises recording the biochemical parameters, time-stamping the biochemical parameters, and organizing the timestamped biochemical parameters according to one or more criteria.

5. The method of claim 1, wherein the breast cavity comprises a breast biopsy cavity.

6. The method of claim 1, wherein the biosensor is not bioabsorbable.

7. The method of claim 1, wherein the biosensor is visible under at least one imaging modality.

8. A method of detecting data related to a human body, the method comprising:
   receiving data collected in real-time from a biosensor implanted in a breast cavity of the human body, wherein the data comprises one or more biochemical parameters and respective values;
   transmitting the data to an external monitoring device located outside of the breast;
   receiving one or more anatomical measurements of a portion of the breast adjacent the biopsy cavity, the anatomical measurements comprising at least one of diameter, length, phenotype, and lesion distribution;
   evaluating the one or more anatomical measurements against detected changes to the one or more biochemical parameters; and
   implementing one or more actions based on the evaluation as a closed feedback loop to enhance the efficacy of a treatment.

9. The method of claim 8, wherein the monitoring system is wirelessly coupled to the biosensor.

10. The method of claim 8, wherein the breast cavity comprises a breast biopsy cavity.

11. The method of claim 8, further comprising:
applying the data to one or more statistical processing models, wherein the one or more statistical processing models are operable to:
compare the data to a set of baseline measurements acquired after implanting the biosensor; and
identify one or more trends in the human body.

12. The method of claim 11, wherein identifying the one or more trends comprises determining an effectiveness of a treatment, wherein the effectiveness of the treatment corresponds to a modification of a neoplastic microenvironment.

13. The method of claim 12, wherein identifying the one or more trends comprises determining a set of biochemical parameters to monitor, and transmitting the determined set of biochemical parameters to the biosensor for monitoring.

14. The method of claim 11, wherein identifying the one or more trends comprises:
applying trend data to an assessment component, wherein the assessment component is operable to perform at least one function selected from the group consisting of:
determining one or more treatments to be applied to a neoplastic microenvironment;
modifying the treatment being applied to the neoplastic microenvironment;
providing at least one of: a notification and a warning; and
generating a report related to the treatment.

15. A method of detecting data related to a human body, the method comprising:
detecting data in real-time with a biosensor implanted in a breast cavity, wherein the data comprises one or more biochemical parameters related to the human body;
collecting the data from the implanted biosensor at a monitoring device discrete from the implanted biosensor;
receiving, at the monitoring device, a user input comprising at least one anatomical measurement of a portion of the breast adjacent the breast cavity, the anatomical measurements comprising at least one of diameter, length, phenotype, and lesion distribution;
evaluating the at least one anatomical measurement against the data; and
implementing at least one action based on the evaluation.

16. The method of claim 15, wherein the implanted biosensor is externally powered.

17. The method of claim 15, wherein the implanted biosensor begins detecting data in response to an activation signal from the monitoring device.

18. The method of claim 17, wherein the activation signal comprises a set of biochemical parameters to be monitored by the implanted biosensor.

19. The method of claim 15, further comprising:
receiving, at a data analysis device, the data;
processing, by the data analysis device, the data to obtain processed data;
using the processed data to determine one or more trends; and
evaluating the one or more trends to assess the breast biopsy cavity.

20. The method of claim 19, wherein identifying the one or more trends comprises generating at least one of: a warning, a notification, a report, and an action item.

* * * * *